(12) United States Patent
Linck et al.

(10) Patent No.: US 6,656,128 B1
(45) Date of Patent: Dec. 2, 2003

(54) DEVICE AND METHOD FOR TREATING HYPERNASALITY

(75) Inventors: Jessica Ann Linck, Cincinnati, OH (US); Jonathon Mark Cross, Cincinnati, OH (US); Ann Wippermann Kummer, Edgewood, KY (US)

(73) Assignee: Children's Hospital Medical Center, Cincinnati, OH (US)

(*) Notice: Subject to any disclaimer, the term of this patent is extended or adjusted under 35 U.S.C. 154(b) by 45 days.

(21) Appl. No.: 10/141,437

(22) Filed: May 8, 2002

(51) Int. Cl.⁷ .............................. A61B 5/08; A61F 5/58
(52) U.S. Cl. .................... 600/538; 600/529; 600/23
(58) Field of Search ..................... 600/538, 529, 600/23, 24, 300, 537

(56) References Cited

U.S. PATENT DOCUMENTS

| | | | |
|---|---|---|---|
| 2,831,181 A | | 4/1958 | Warner |
| 3,752,929 A | | 8/1973 | Fletcher |
| 3,906,936 A | | 9/1975 | Habal |
| 4,106,505 A | | 8/1978 | Salter et al. |
| 4,143,648 A | * | 3/1979 | Cohen et al. .................. 600/23 |
| 4,335,276 A | | 6/1982 | Bull et al. |
| 4,519,399 A | | 5/1985 | Hori |
| 4,579,124 A | | 4/1986 | Jentges |
| 4,862,503 A | | 8/1989 | Rothenberg |
| 5,103,834 A | * | 4/1992 | Rineau ........................ 600/537 |
| 5,269,296 A | | 12/1993 | Landis |
| 5,340,316 A | | 8/1994 | Javkin et al. |
| 5,647,834 A | * | 7/1997 | Ron ............................ 600/23 |
| 6,213,955 B1 | | 4/2001 | Karakasoglu et al. |
| 6,298,850 B1 | | 10/2001 | Argraves |
| 6,308,798 B1 | | 10/2001 | Rashman et al. |

OTHER PUBLICATIONS

Ann W. Kummer, Cleft Palate & Craniofacial Anomalies, Effects on Speech and Resonance (2001) pp. 274–290, 311–328, Singular/Thompson Learning, San Diego.

A Noninvasive Technique for Detecting Hypernasal Speech Using a Nonlinear Operator, IEEE Transactions on Biomedical Engineering, vol. 43, No. 1. Jan. 1996, pp. 35–45.

Managing Speech Disorders: How to Develop Your Non–Instrumental Clinical Skills for Assessing Velopharyngeal Function, available on webpage; http://www.choa.org/craniofacial/speech-4,shtml, pp. 1–6 on Apr. 8, 2002.

* cited by examiner

*Primary Examiner*—Max F. Hindenburg
*Assistant Examiner*—Navin Natnithithadha
(74) *Attorney, Agent, or Firm*—Donald E. Hasse; Daniel F. Nesbitt; Eric W. Guttag

(57) ABSTRACT

A device for evaluating or treating a patient for hypernasality or nasal air emission during speech is disclosed. The device contains a nosepiece for collecting nasal auditory output from the patient, a first listening device connected to the nosepiece to enable a therapist to receive the auditory output, and a second listening device connected to the nosepiece to enable the patient to receive the auditory output. Also disclosed is a method for evaluating or treating a patient for hypernasality or nasal air emission during speech using the above device.

23 Claims, 2 Drawing Sheets

DEVICE AND METHOD FOR TREATING HYPERNASALITY

TECHNICAL FIELD

The present invention relates to a device that can be used in the evaluation or treatment of patients for hypernasality or nasal air emission during speech. The invention also relates to a method for evaluating or treating patients for such a condition.

BACKGROUND OF THE INVENTION

Hypernasality and nasal air emission are speech characteristics due to a form of velopharyngeal dysfunction (also called velopharyngeal insufficiency or incompetence). In normal speech, the velum or soft palate elevates and closes against the posterior pharyngeal wall (the back wall of the throat). At the same time, the lateral pharyngeal walls move inward. These movements result in closure of the velopharyngeal valve, which closes off the nasal cavity from the oral cavity for normal speech. When the valve does not close completely, due to either structural or neurological abnormalities, air and sound escape into the nasal cavity during speech. This is a common problem for patients with a history of cleft palate, submucous cleft or various craniofacial syndromes. It is also commonly seen in patients with neuro-motor problems that affect muscle movement of velum and pharyngeal walls.

In evaluating hypernasality and nasal air emission, most speech pathologists rely on their ear for the assessment. Some have reported the use of a straw or listening tube to enhance the auditory signal. This can be accomplished by placing one end of the straw or tube at the tip of the patient's nostril and the other end in the examiner's ear. While this simple device works well in magnifying the auditory signal, the tube does not allow for hands-free use and only one person can listen at a time. In a therapeutic setting, where auditory biofeedback can greatly enhance therapy progress, it would be beneficial for the patient to be able to listen to the amplified sound coming from the nasal cavity at the same time as the therapist.

Other methods for evaluating hypernasality are more complex and expensive to use. Such methods may utilize spirometry measurement, airflow measurement with an anesthesia mask, ultrasonic devices, transducer devices, and oscilloscopic imaging. Various methods and devices for evaluating hypernasality or nasal airflow are disclosed in the following patents.

U.S. Pat. No. 3,752,929, issued to Fletcher on Aug. 14, 1973, describes a process and apparatus to independently measure auditory output from the nose and mouth. The apparatus uses microphones placed near the oral and nasal orifices. Quantitative electronic output for the nose and mouth are compared to determine the degree of nasality.

U.S. Pat. No. 4,862,503, issued to Rothenberg on Aug. 29, 1989, describes an apparatus and technique for extracting voice parameters from oral or combined oral and nasal airflow, using a tightly fitting mask. Voice parameters are detected and recorded with an electronic device.

U.S. Pat. No. 6,213,955 B1, issued to Karakasoglu et al. on Apr. 10, 2001, discloses an apparatus for measuring respiratory airflow from the nose and/or mouth of a patient, comprising a device having at least one acoustic duct receiving respiratory airflow. A sensor is exposed to the acoustic duct and senses turbulence, vibration and/or sound in the airflow in the acoustic duct to provide an electric output signal. Despite these advances in the art, there is a continuing need for a simple and effective device for evaluating and/or treating patients for hypernasality or nasal air emission during speech.

SUMMARY OF THE INVENTION

The present invention relates to a device for evaluating or treating a patient for hypernasality or nasal air emission during speech, said device comprising:

(a) a nosepiece for collecting nasal auditory output from the patient;

(b) a first listening device connected to the nosepiece to enable a therapist to receive the auditory output; and (c) a second listening device connected to the nosepiece to enable the patient to receive the auditory output.

The invention also relates to a method for evaluating or treating a patient for hypernasality or nasal air emission during speech by using the above device.

BRIEF DESCRIPTION OF THE DRAWINGS

The foregoing aspects and advantages of the invention will be better understood from the following detailed description of the invention with reference to the accompanying drawings, in which.

DETAILED DESCRIPTION OF THE INVENTION

Figure 1:
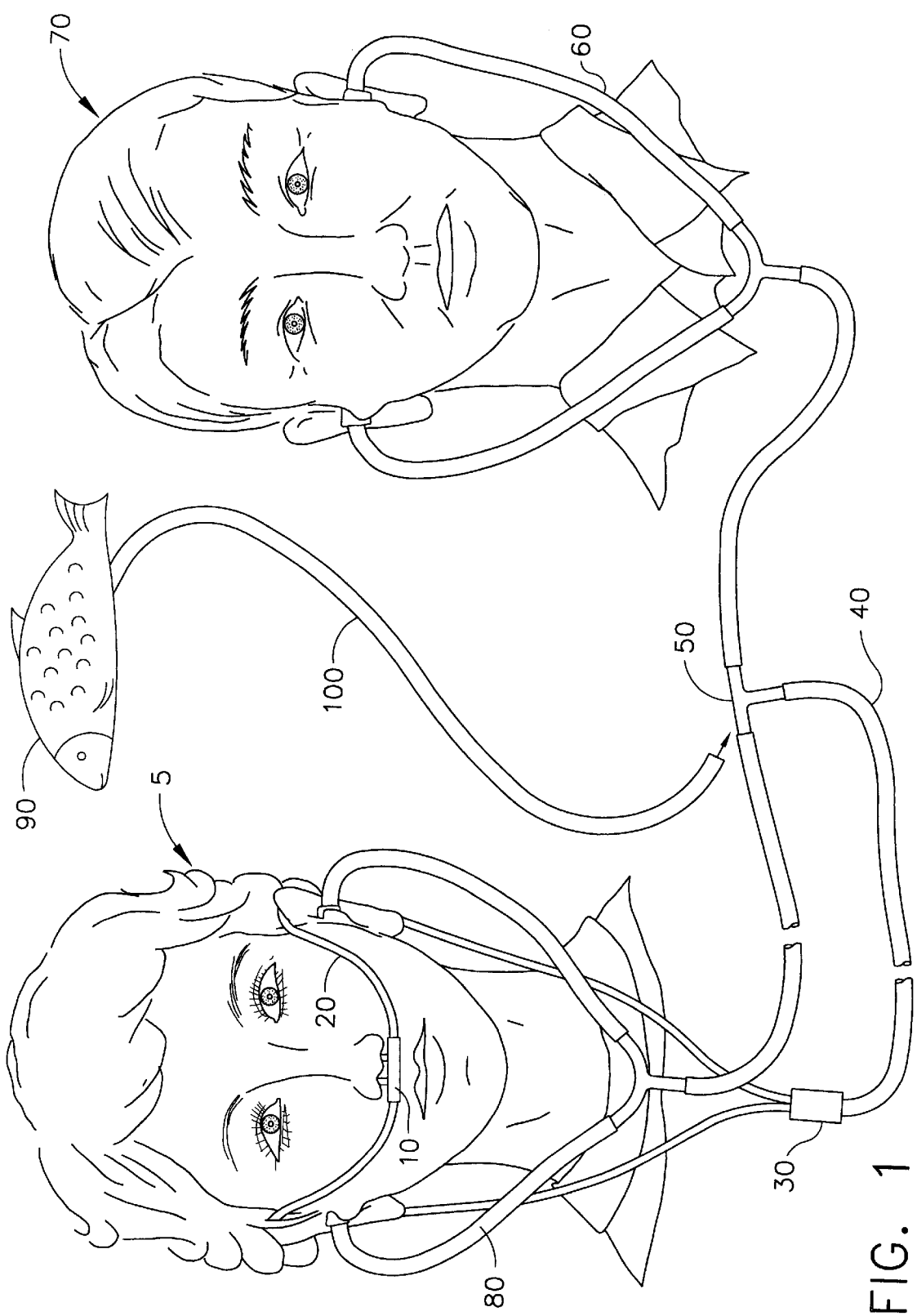
FIG. 1 is a front elevational view of a device of the present invention mounted on a patient's head with stethoscopes used as listening devices to enable a therapist and the patient to hear the nasal auditory output from the patient.

As used herein, the term "comprising" means various components, capabilities and/or steps can be conjointly employed in the present invention. Accordingly, the term "comprising" encompasses the more restrictive terms "consisting essentially of" and "consisting of".

As used herein, the term "patient" refers to any person being evaluated or treated for hypernasality or nasal air emission during speech.

As used herein, the term "therapist" refers to any person evaluating or treating a patient for hypernasality or nasal air emission during speech, including a physician, speech pathologist, speech therapist, clinician, parent or other person evaluating or treating the patient.

The present invention provides a device and a method for evaluating or treating a patient for hypernasality or nasal air emission during speech. The device comprises a nosepiece for collecting auditory output from the patient. The nosepiece can be any suitable device known in the art for collecting auditory output from a patient. The nosepiece may cover all or part of the nose, or it may fit in or near one or both nostrils. The nosepiece should not cover the mouth, or otherwise muffle or distort sounds coming from the patient's nasal cavity. The nosepiece may be a mask or assembly, such as disclosed in U.S. Pat. No. 2,831,181, Warner; or a nose mask such as disclosed in U.S. Pat. No. 3,906,936, Habal; both incorporated herein by reference.

In one embodiment of the invention, the nosepiece is a nasal cannula. A nasal cannula typically comprises a nasal assembly, with a hollow main body having two directed orifices near or in a patient's nostrils. Typically, the orifices are placed at the end of nasal extension tubes extending upwardly from a main body portion and in communication with the main body. In another embodiment of the invention, flexible tubing is connected to the cannula nosepiece that is held in place by extending the tubing from the patient's nasal area behind the patient's ears. The flexible tubing can be bent or draped downward behind the ears to run generally along the jaw area, and can be held in place by an adjustable slip loop or a cinch tightened below the chin. In use, the nosepiece of a cannula typically is placed against the nasal septum, and tension is applied against it to secure the nosepiece in place. Nasal cannulas and methods for securing them are disclosed in U.S. Pat. No. 4,106,505, Salter et al.; U.S. Pat. No. 6,213,955 B1, Karakasoglu, et al.; U.S. Pat. No. 6,298,850 B1, Argraves; and U.S. Pat. No. 5,269,296, Landis; all incorporated herein by reference.

The device of the present invention also comprises a first listening device connected to the nosepiece to enable the therapist to receive the auditory output from the patient. The first listening device may be directly connected to the nosepiece, or indirectly connected to it, for example, by one or more flexible tubes and/or connectors. The first listening device may be any suitable device for receiving the auditory output from the patient. The first listening device typically has at least one earpiece that fits in, adjacent to, or over the therapist's ear to improve reception of the nasal auditory output while minimizing or blocking out other sounds. The first listening device typically has two earpieces to better enable the therapist to hear the nasal auditory output and block out other sounds. In one embodiment, the first listening device comprises headphones or a headset that fits over the therapist's ears, and is connected to the nosepiece by flexible tubing. In another embodiment of the invention, the first listening device is a standard stethoscope in which the metal drum or head is removed and the flexible tubing is connected to the nosepiece. A simple stethoscope may thus comprise one or typically two earpieces connected to flexible tubing for transmitting sound. A suitable stethoscope is disclosed in U.S. Pat. No. 6,308,798, Rashman, et al; U.S. Pat. No. 6,202,784, Alatriste; and U.S. Pat. No. 5,952,618, Deslauriers; all incorporated herein by reference.

The device herein further comprises a second listening device connected to the nosepiece to enable the patient to also receive the auditory output. The second listening device may be directly connected to the nosepiece, or indirectly connected to it, for example, by one or more flexible tubes and/or connectors. The second listening device may be any suitable device for receiving the auditory output from the nosepiece. The second listening device typically has at least one earpiece that fits in, adjacent to, or over the patient's ear to improve reception of the nasal auditory output while minimizing or blocking out other sounds. The second listening device typically has two earpieces to better enable the patient to hear the nasal auditory output and block out other sounds. In one embodiment, the second listening device comprises headphones or a headset that fits over the patient's ears, and is connected to the nosepiece by flexible tubing. Alternatively, the headphones or headset may be part of a one-piece mask also containing the nosepiece. In another embodiment, the second listening device is a second stethoscope, such as described above. Alternatively, the second listening device can be a toy, such as a hollow plastic or rubber toy that allows the passage of air and sound when held in or near the patient's ear. Such a toy can enhance the interest of young children in therapy using the present invention. To further enhance the interest of children, the first listening device may also be a matching or complimentary toy used by the therapist.

In one embodiment of the invention, the nosepiece and first listening device are connected by a first flexible tubing having a proximal end connected to the nosepiece and a distal end connected to the first listening device. The flexible tubing should be of sufficient length to allow for comfortable spacing between the patient and the therapist. The nosepiece and the second listening device may also be connected by the same or a different flexible tubing having a proximal end connected to the nosepiece and a distal end connected to the second listening device. Preferably, the distal end of the first flexible tubing is connected to the first listening device and to the second listening device via a multi-port connector. For example, a three-port connector, such as a three-way T or Y shaped connector, can be used to connect the first flexible tubing to the first and second listening devices. If an additional listening device is desired, a four-port connector may be used.

In another embodiment, the device of the invention comprises:

(a) a nasal cannula for collecting nasal auditory output from the patient;

(b) a first flexible tubing connected to both ends of the nasal cannula; (c) a second flexible tubing connected to the free ends of the first flexible tubing by a first connector;

(d) a first stethoscope connected to the second flexible tubing by a multi-port connector to enable a therapist to receive the auditory output from the patient; and (e) a second listening device connected to the second flexible tubing by the multi-port connector to enable the patient to simultaneously receive the auditory output.

The device of the present invention provides a simple, inexpensive and effective means for a therapist to obtain nasal auditory output from a patient. The device maintains the basic principle of a listening tube with magnification of the nasal auditory output. It also allows for two or more listeners (for example, a speech pathologist and the patient, or a parent and the patient) to simultaneously hear the amplified sound coming from the patient's nasal cavity. This provides direct and immediate auditory biofeedback to the patient that can enhance therapy progress. Such direct feedback typically is more useful to the patient than a visual representation of the nasal sounds produced by electronic devices disclosed in the art. The device of the invention also allows for hands-free use, freeing the patient and therapist to concentrate on the nasal auditory output. The device is portable so that the patient can take it home for additional practice and use, which increases the possibility of correction of hypernasality or nasal air emission. Since the device is simple and inexpensive to manufacture, several devices can be purchased and used at home, at school, or at other convenient locations. The device can also be designed with a variety of fun nosepieces and earpieces to enhance the interest of young children in therapy.

The device of the present invention, and each component thereof, may be formed of a suitable medical grade rubber or plastic such as polyurethane, polyvinyl chloride or silicone. Components of the device may also include metal parts for increased durability and strength. For example, the connectors and/or headsets, if present, may contain metal parts. The device, and each component thereof, can be formed of materials that are relatively flexible to accommodate the contours of the face so that the device is comfortable when worn by the patient and the therapist. Flexible components, such as tubing, connectors, nosepiece and earpieces, also provide some freedom of movement for the therapist and patient that can enhance comfort and allow them to concentrate on listening to the nasal auditory output from the patient.

For a better understanding of the invention, reference is now made to FIG. 1 of the drawings. This figure represents a device in which a standard nasal cannula 10 inserts into the nostrils of patient 5. Silicon tubing 20 is connected to both sides of the cannula, and is looped around the patient's ears to secure the nasal cannula to the face. The distal ends of the tubing 20 are connected via first connector 30 to one end of a second, larger diameter silicon tubing 40 that attaches at its other end to one arm of a plastic three-way connector 50. After removing the metal drum from the bottom of two stethoscopes, the flexible tubing of each stethoscope is attached to one of the two remaining arms of connector 50. Once this is done, there are two sets of listening devices, a first stethoscope 60 for therapist 70 and a second stethoscope 80 for patient 5. First stethoscope 60 and second stethoscope 80 enable therapist 70 and patient 5 to simultaneously listen to the nasal auditory output from the patient. In the case of a child who is reluctant to use a stethoscope, a hollow plastic toy 90, attached to connector 50 by flexible tubing 100, and pierced to allow the passage air and sound, can be substituted for second stethoscope 80. The toy can be held near one of the patient's ears so the patient can hear the nasal auditory output. A second toy (not shown) or other listening device can be substituted for first stethoscope 60 and held near one of the therapist's ears to enable the therapist to hear the nasal auditory output.

Figure 2:
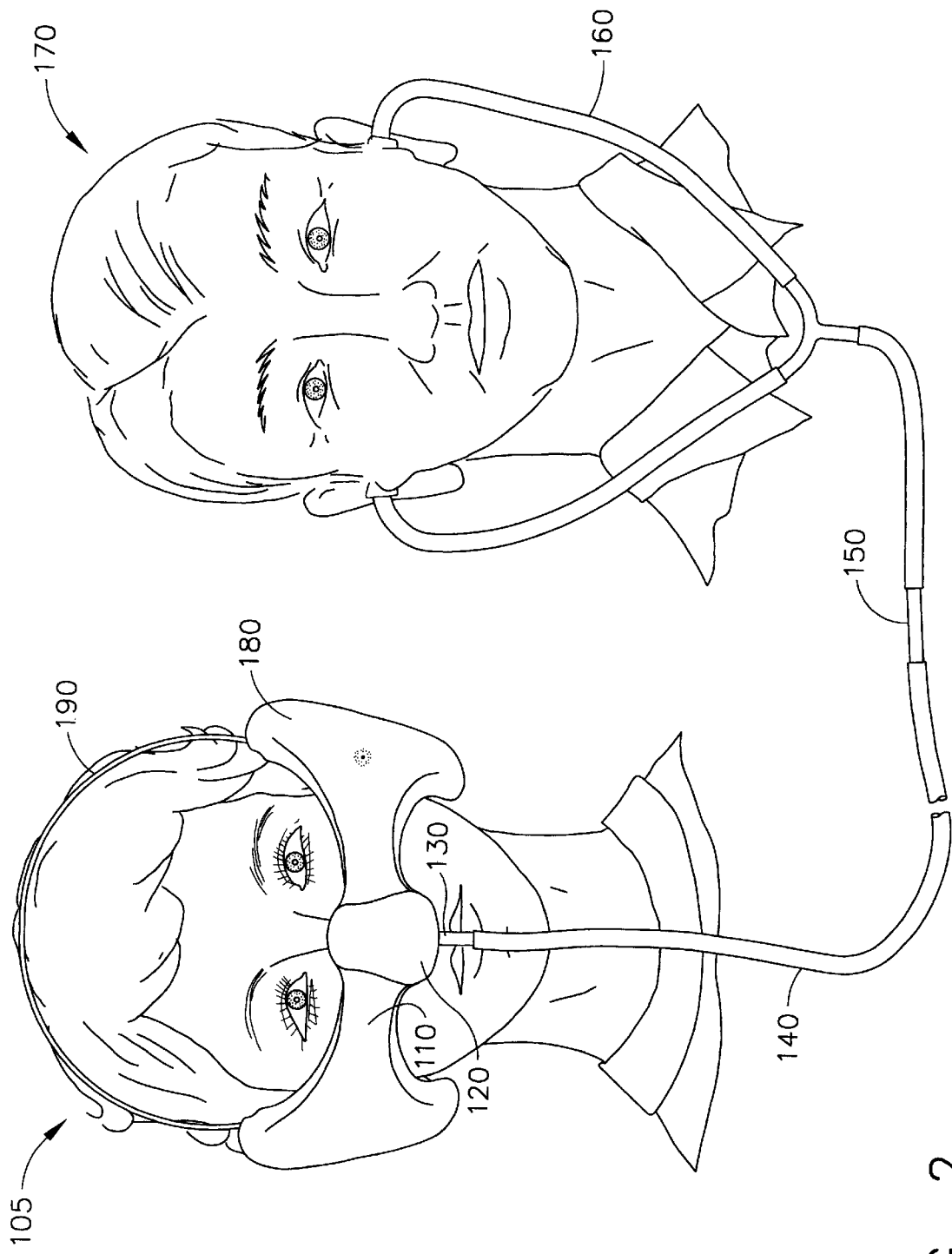
FIG. 2 is a front elevational view of another device of the invention in which a stethoscope and a one-piece mask covering the nose and ears of a patient enable a therapist and the patient to hear the nasal auditory output from the patient.

FIG. 2 shows another device of the present invention in which a one-piece mask 110 covers the nose and ears of patient 105. Mask 110 contains nosepiece 120, which is connected to flexible tubing 140 by first connector 130. The distal end of flexible tubing 140 is connected to the flexible tubing of stethoscope 160 by second connector 150. This enables therapist 170 to listen to the nasal auditory output from patient 105. The nasal auditory output is simultaneously transmitted to the earphones 180 of mask 110, which is secured to the face of patient 105 by strap 190. The nasal auditory output can be transmitted from nosepiece 120 to earphones 180 via a channel (not shown) on the inside of mask 110, or via flexible tubing (not shown) extending on the inside or outside of mask 110 from nosepiece 120 to earphones 180. In another embodiment, a nasal cannula such as in FIG. 1 can be located inside nosepiece 120, or it can be used in place of nosepiece 120, to collect the nasal auditory output from the patient. Alternatively, such a nasal cannula can be connected to a headset with earphones that enable the patient to hear the nasal auditory output.

The present invention also comprises a method for evaluating or treating a patient for hypernasality or nasal air emission during speech, said method comprising:

(a) collecting nasal auditory output from the patient through a nosepiece;

(b) enabling a therapist to receive the auditory output through a first listening device connected to the nosepiece; and (c) enabling the patient to receive the auditory output through a second listening device connected to the nosepiece.

The above method of the invention can be practiced using the devices described herein and other devices of the invention.

The foregoing invention has been described in terms of various embodiments. However, it will be apparent to those skilled in the art that modifications and variations can be made in the disclosed devices and methods without departing from the scope or spirit of the invention. The specification and examples are exemplary only, while the true scope of the invention is defined by the following claims.

What is claimed is:

1. A device for evaluating or treating a patient for hypernasality or nasal air emission during speech, said device comprising:

(a) a nosepiece for collecting nasal auditory output from the patient;

(b) a first listening device connected to the nosepiece to enable a therapist to receive the auditory output; and (c) a second listening device connected to the nosepiece to enable the patient to receive the auditory output.

2. A device according to claim 1 further comprising a first flexible tubing having a proximal end connected to the nosepiece and a distal end connected to the first listening device.

3. A device according to claim 2 wherein the distal end of the first flexible tubing is connected to the first listening device and to the second listening device via a multi-port connector.

4. A device according to claim 3 wherein the first listening device is a first stethoscope.

5. A device according to claim 4 wherein the second listening device is a second stethoscope.

6. A device according to claim 4 wherein the second listening device is a toy.

7. A device according to claim 1 wherein the nosepiece is a nasal cannula.

8. A device according to claim 7 further comprising a first flexible tubing having a proximal end connected to the nasal cannula and a distal end connected to the first listening device.

9. A device according to claim 8 wherein the first listening device is a first stethoscope.

10. A device according to claim 9 wherein the distal end of the first flexible tubing is connected to the first stethoscope and to the second listening device via a multi-port connector.

11. A device according to claim 10 wherein the second listening device is a second stethoscope.

12. A device according to claim 1 wherein the nosepiece and the second listening device are part of a one-piece mask that covers the nose and ears of the patient.

13. A device according to claim 12 wherein the first listening device is a stethoscope.

14. A device according to claim 13 wherein flexible tubing connects the nosepiece to the stethoscope.

15. A device for evaluating or treating a patient for hypernasality or nasal air emission during speech, said device comprising:

(a) a nasal cannula for collecting nasal auditory output from the patient;

(b) a first flexible tubing connected to both ends of the nasal cannula;

(c) a second flexible tubing connected to the free ends of the first flexible tubing by a first connector;

(d) a first stethoscope connected to the second flexible tubing by a multi-port connector to enable a therapist to receive the auditory output from the patient; and (e) a second listening device connected to the second flexible tubing by the multi-port connector to enable the patient to simultaneously receive the auditory output.

16. A device according to claim 15 wherein the second listening device is a stethoscope.

17. A device according to claim 15 wherein the second listening device is a toy.

18. A method for evaluating or treating a patient for hypernasality or nasal air emission during speech, said method comprising:
(a) collecting nasal auditory output from the patient through a nosepiece;
(b) enabling a therapist to receive the auditory output through a first listening device connected to the nosepiece; and
(c) enabling the patient to receive the auditory output through a second listening device connected to the nosepiece.

19. A method according to claim 18 wherein the auditory output is transmitted to the therapist via a first flexible tubing having a proximal end connected to the nosepiece and a distal end connected to the first listening device.

20. A method according to claim 19 wherein the first listening device is a first stethoscope.

21. A method according to claim 20 wherein the distal end of the first flexible tubing is connected to the first stethoscope and to the second listening device via a multi-port connector.

22. A method according to claim 21 wherein the nosepiece is a nasal cannula.

23. A method according to claim 22 wherein the second listening device is a second stethoscope.

* * * * *